(12) United States Patent
Schultz

(10) Patent No.: US 6,765,112 B1
(45) Date of Patent: Jul. 20, 2004

(54) FLUORINATED ONIUM SALTS

(75) Inventor: James A. Schultz, Woolwich Township, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/396,942

(22) Filed: Mar. 25, 2003

(51) Int. Cl.$^7$ ............................................. C07C 309/00
(52) U.S. Cl. ..................... 562/115; 562/113; 562/114
(58) Field of Search ........................ 562/30, 113, 114, 562/115, 124; 568/9

(56) References Cited

U.S. PATENT DOCUMENTS

| | | | |
|---|---|---|---|
| 5,051,330 A | | 9/1991 | Alexandrovixh et al. |
| 6,194,497 B1 | | 2/2001 | Willems et al. |
| 6,372,829 B1 | * | 4/2002 | Lamanna et al. ............ 524/99 |
| 6,406,830 B2 | * | 6/2002 | Inoue et al. ............ 430/270.1 |

FOREIGN PATENT DOCUMENTS

| DE | 3347378 | * | 7/1985 |
|---|---|---|---|
| WO | WO 01/49925 A | | 7/2001 |

OTHER PUBLICATIONS

Inorganic Chemistry by Abney et al vol. 26 pp. 2638–2643 1987.*
CA:135:93892 abs of WO2001049925 Jul. 2001.*
CA:139:180842 abs of WO 2003066724 Aug. 2003.*
CA:138:237891 abs of WO 200302683 Mar. 2003.*

* cited by examiner

Primary Examiner—Jean F. Vollano

(57) ABSTRACT

A process that can be used for manufacturing a tetraalkylonium perfluoroalkylsulfonate is provided. The process comprises contacting a tetraalkylonium halide with a metal perfluoroalkyl sulfonate to produce a mixture; allowing the second mixture to produce an aqueous upper layer and a separate lower liquid layer; separating the lower liquid layer from the upper aqueous layers to produce a product layer; optionally washing the product layer with 1 to 10 volumes of water, based on the volume of the product layer at a temperature of about 50° C. to about 100° C. to produce a washed product layer; and drying the product layer or washed product.

18 Claims, No Drawings

FLUORINATED ONIUM SALTS

FIELD OF THE INVENTION

This invention relates to fluorinated onium sulfonate, especially fluorinated onium sulfonate, antistats and to a process for their preparation.

BACKGROUND OF THE INVENTION

Typical synthetic organic polymers are not good conductors of electricity, giving rise to a buildup of static charges. These in turn cause the polymers to attract dust or dirt, cling to other surfaces, and cause other difficulties in their processing or application. Phosphonium sulfonates, for example, have been found to be effective antistats when incorporated in such organic polymers, particularly those wherein the sulfonate moiety contains a perfluorinated organic chain. Such phosphonium sulfonates have also been found useful in improving the electrostatic transfer efficiency of toner powders used in electrostatic copying. Most know processes for producing a tetraalkylonium perfluoroalkylsulfonate require one or two ion exchange steps. Though U.S. Pat. No. 5,051,330 discloses reacting $M^+(R^1)(R^2)(R^3)(R^4)X^-$ with $Li^+(R^6)SO_3^-$ to produce a fluorinated onium sulfonate $M^+(R^1)(R^2)(R^3)(R^4)(R^6SO_3^-)$, the patent does not disclose or suggest any reaction conditions. Nor does it disclose or suggest how the reaction is driven to completion. Nor does it disclose or suggest the reaction of a perfluoroalkyl sulfonate salt with a tetraalkyl phosphonium halide. Therefore, there is a need to develop a process for the manufacture of a tetraalkylonium perfluoroalkyl sulfonate in which the process does not include an ion exchange step.

SUMMARY OF THE INVENTION

This invention provides a process that can be used for manufacturing a tetraalkylonium perfluoroalkyl sulfonate. The process comprises (1) combining an aqueous solution of a tetraalkylonium halide and an aqueous solution of a metal perfluoroalkyl sulfonate to produce a mixture; (2) allowing the mixture to form an aqueous upper phase and a separate liquid lower phase; (3) separating the lower phase from the upper phase; and (4) drying the lower phase or washed lower phase, preferably under vacuum conditions. The process can comprise, after step (3) and before step (4) washing the lower layer with water to produce a washed lower phase, which can be then dried.

DETAILED DESCRIPTION OF THE INVENTION

According to the invention, the term "tetraalkylonium halide" refers to "tetraalkylammonium halide", "tetraalkylphosphonium halide", or both, preferably "tetraalkylphotphonium halide". Though any halide can be used, the preferred halide is bromide. The metal in "metal perfluoroalkyl sulfonate" can be an alkali or alkaline earth metal, preferably alkali metal, and most preferably potassium.

The alkyl group in tetraalkylonium halide and metal perfluoroalkyl sulfonate can independently contain 1 to about 10, preferably about 3 to about 5, carbon atoms. The preferred tetraalkylonium halide is tetrabutyl phosphonium bromide and the preferred metal perfluoroalkyl sulfonate is perfluorobutane sulfonate for the product produced there from has desired properties.

The tetraalkylonium halide and metal perfluoroalkyl sulfonate can be commercially available or produced by any methods known to one skilled in the art. For example, potassium perfluorobutane sulfonate can be made by electrochemical fluorination of butanethiol and tetrabutylphosphonium bromide can be made by free radical addition of 1-butene to phosphine ($PH_3$) followed by guarternization with butyl bromide.

In the preferred process, two solutions are first prepared. In solution A, a tetrabutylonium halide is dissolved in, preferably a minimum amount of water to dissolve it at ambient temperature. For example, about 400 ml water may be used for one mole of halide.

Similarly in solution B, a metal perfluoroalkyl sulfonate is also preferably dissolved in a minimum amount of water to achieve full solubility. A temperature of about 60° C. is preferably used to aid solution. For example, 2 liters of water can dissolve one mole of the potassium sulfonate.

Wishing not to be bound by theory, the use of more water than the minimum amounts may unnecessarily reduce the effective charge size.

Solution A can then be slowly combined with solution B to produce a combination. The combination is preferably mixed under at a temperature of about 50° C. to about 100° C. such as, for example, about 60° C. to about 70° C., to facilitate the production of a tetrabutylonium halide-metal perfluoroalkyl sulfonate mixture. The mixing can be facilitated using a mechanical means such as, for example, agitation for a period of time sufficient to produce two phases, typically about 1 minute to about 1 hour.

Thereafter, the phases can be separated by any means known to one skilled in the art such as, for example, decantation, centrifugation, or other means. The temperature of the two phases at separation may be between 0° C. and 100° C., preferably below about 70° C., more preferably, about 55° C. to about 60° C., to minimize loss of product due to solubility. The lower layer, or product layer, can then be recovered.

The recovered product layer is preferably washed with water, at about 1 to about 10 volumes of the product layer, to remove any contaminated metal halide. Washing can be carried out at a temperature of about 50° C. to about 100° C. A larger amount of water, a higher temperature, or both may increase product losses because of increased solubility. A smaller amount of water, a lower temperature, or both may result in a product containing an unacceptable amount of metal halide.

The product can then be dried under an inert atmosphere to remove any residual water present, preferably at a temperature above about 50° C. Preferably the product is sparged or the surface gas purged with nitrogen or other inert gas. More preferably the sparging is carried out under a vacuum.

Also according to the invention, step 1 of the process can also be carried out by combining a dry tetraalkylonium halide and a dry metal perfluoroalkyl sulfonate to produce a dry combination followed by adding minimum amount of water, as disclosed above, to the dry combination to produce the mixture. Step 1 of the process can also be carried out by combining a tetraalkylonium halide and a potassium perfluoroalkyl sulfonate in which either the tetraalkylonium halide or the potassium perfluoroalkyl sulfonate may be an aqueous solution while the other is a dry powder along with a minimum amount of water as disclosed above for making the mixture.

The metal perfluoroalkyl sulfonate disclosed above may be replaced by a combination of approximately equimolar of perfluoroalkyl sulfonic acid and metal hydroxide.

The following examples are provided to illustrate, and are not to be construed to unduly limit the scope of, the invention.

EXAMPLES

Example 1

Phase Separation by Decantation of Liquid Layers

Potassium perfluorobutanesulfonate (PFBSK; 678 g, 2 moles; obtained from Miteni, Trissino, Italy) was dissolved in 3 liters of water. A 75% solution containing tetrabutylphosphonium bromide (678 g, 2 moles; obtained from Aldrich Chemicals, Milwaukee, Wis., USA) was slowly added at 70° C. for 1 hour and the phases were allowed to separate. The upper layer was drawn off, and replaced with 3 liters of fresh deionized water. The solutions were agitated at 65° C. for 20 minutes and allowed to settle. The upper layer was drawn off, and the wash process repeated. The product was dried at 100° C. and 25" (inch) of vacuum (165 KPa) to give 1085 g (97%) of a product containing 2 ppm (parts per million by weight) potassium, 0.02 weight % water, and having a Differential Scanning Calorimetry (DSC) melting point of 71.8° C.

Example 2

Decantation by Freezing out the Product Layer

PFBSK (339 g, 1 mole) was dissolved in 1500 ml water by warming to 62° C. Tetrabutylphosphonium bromide (339 g, 1 mole) was dissolved in 400 ml water at room temperature (about 25° C.). Phosphonium bromide solution was slowly added to the PFBSK solution with agitation. A lower, oily phase separated. Agitation was continued for 20 minutes, and the solution was allowed to cool to room temperate, freezing the bottom product layer. The upper aqueous phase was decanted, and replaced with 1500 ml distilled water. The resulting mixture was heated to 80° C., agitated for 20 min, and again allowed to freeze. The water was decanted, and 1500 ml fresh water was added. The mixture was again heated to 80° C., and agitated 20 min. The product layer was allowed to freeze, and the water decanted. The product was then melted and dried under 13 inch Hg vacuum (566 kPa) at 88° C. The product was collected giving 532 g (95% yield) tetrabutyl phosphonium perfluorobutanesulfonate having an ionic potassium content of <7 ppm by weight.

Example 3

Direct Combination of Solid Ingredients

Tetrabutyl phosphonium bromide (100 g, 0.295 mole) and PFBSK (100 g, 0.295 mole) were mixed as dry powders. Water (400 ml) was added and the mixture heated to 80° C. for 3 hours.

The mixture was allowed to cool to room temperature and the aqueous phase decanted from the frozen product phase. Water (400 ml) was added, the mixture heated to 80° C., and agitated for 20 minutes. The aqueous phase was again decanted from the frozen product phase. Water (400 ml) was again added and the melt-wash-freeze-decant process repeated. The product was then dried at 80° C. and 25 inches Hg vacuum (165 KPa) to give tetrabutylphosphonium perfluorobutanesulfonate, 164 g, 74% with a potassium level of 2.2 ppm and a moisture content of 0.02%, both by weight.

Example 4

Into a 100 gal reactor were placed 116.9 pounds (53.0 Kg, 156.5 moles) PFBSK and 62.7 gallons (237 liters) water. The solution was heated to 60° C. Then 147 pounds (50.0 Kg, 147 moles) of a 75% solution containing tetrabutyl phosphonium bromide (obtained from Cytec, Niagara Falls, Ontario, Canada) was added over a period of 20 minutes. The solutions were mixed for 30 minutes, and the phases allowed to separate. The lower liquid product layer was transferred to a second vessel, and contacted with 62 gallons (234.4 liters) of additional 70° C. water. Agitation was stopped, the phases allowed to separate, and the lower phase was decanted back to the first reactor. The product was washed a total of 5 times in like manner. After the fifth wash, 11 gallons (41.6 liters) of water was added and distilled to remove low boiling phosphorus containing impurities, then the product was dried at 80° C. and under vacuum. The product was discharged to a stainless steel pan and allowed to solidify, then broken up and placed in pails. Yield was 177 pounds (80.3 Kg, 144 moles, 98%). The product contained 5 ppm potassium and had a melting point of 68.9 C. by DSC.

What is claimed is:

1. A process comprising (1) combining an aqueous solution of a tetraalkylonium halide and an aqueous solution of a metal perfluoroalkyl sulfonate to produce a mixture; (2) allowing said mixture to form an aqueous upper layer and a separate liquid lower layer; (3) separating and recovering said lower layer from the upper layer to produce a product layer; and (4) drying said product layer wherein said tetraalkylonium halide is tetraalkylammonium halide or tetraalkylphosphonium halide and said metal perfluoroalkyl sulfonate is an alkali metal perfluoroalkyl sulfonate or an alkaline earth metal perfluoroalkyl sulfonate.

2. A process according to claim 1 wherein said product layer in step (3) is further washed with water.

3. A process according to claim 2 wherein said separating is carried out at a temperature of about 0° C. to about 100° C. and said product layer is washed at a temperature of 50° C. to 100° C.

4. A process according to claim 2 wherein said separating and recovering in step (3) is carried out by solidifying said lower layer to produce said product layer followed by removing said upper layer.

5. A process according to claim 1 wherein said tetraalkylonium halide is tetrabutylphosphonium bromide and said metal perfluoroalkyl sulfonate is potassium perfluorobutyl sulfonate.

6. A process according to claim 2 wherein said tetraalkylonium halide is tetrabutylphosphonium bromide and said metal perfluoroalkyl sulfonate is potassium perfluorobutyl sulfonate.

7. A process according to claim 3 wherein said tetraalkylonium-halide is tetrabutylphosphonium bromide and said metal perfluoroalkyl sulfonate is potassium perfluorobutyl sulfonate.

8. A process according to claim 4 wherein said tetraalkylonium halide is tetrabutylphosphonium bromide and said metal perfluoroalkyl sulfonate is potassium perfluorobutyl sulfonate.

9. A process for manufacturing a tetraalkylonium perfluoroalkylsulfonate comprising (1) contacting a tetraalkylonium halide with a metal perfluoroalkyl sulfonate to produce a mixture wherein said tetraalkylonium halide or said metal perfluoroalkyl sulfonate is, or both are, in dry form; (2) adding water to said mixture followed by heating at a temperature of about 50° C. to about 100° C. to produce a second mixture; (3) allowing said second mixture to produce an aqueous upper layer and a separate lower liquid layer; (4) separating and recovering said lower liquid layer from said upper aqueous layers at a temperature of about 0° C. to about 100° C. to produce a product layer; (5) washing said product layer with 1 to 10 volumes of water, based on the volume of said product layer at a temperature of about 50° C. to about 100° C. to produce a washed product layer; and (6) drying said washed product wherein said tetraalkylonium halide is tetraalkylammonium halide or tetraalkylphosphonium halide and said metal perfluoroalkyl sulfonate is an alkali metal perfluoroalkyl sulfonate or an alkaline earth metal perfluoroalkyl sulfonate.

10. A process for according to claim 9 wherein said tetraalkylonium halide and said metal perfluoroalkyl sulfonate are in dry form.

11. A process for according to claim 9 wherein said tetraalkylonium halide is in dry form and said metal perfluoroalkyl sulfonate is in solution.

12. A process for according to claim 9 wherein said tetraalkylonium halide is in solution and said metal perfluoroalkyl sulfonate is in dry form.

13. A process according to claim 10 wherein said tetraalkylonium-halide is tetrabutylphosphonium bromide and said metal perfluoroalkyl sulfonate is potassium perfluorobutyl sulfonate.

14. A process according to claim 11 wherein said tetraalkylonium halide is tetrabutylphosphonium bromide and said metal perfluoroalkyl sulfonate is potassium perfluorobutyl sulfonate.

15. A process according to claim 12 wherein said tetraalkylonium halide is tetrabutylphosphonium bromide and said metal perfluoroalkyl sulfonate is potassium perfluorobutyl sulfonate.

16. A process according to claim 13 wherein said separating and recovering in step 4 is carried out by solidifying said lower layer to produce said product layer followed by removing said upper layer.

17. A process according to claim 14 wherein said separating and recovering in step 4 is carried out by solidifying said lower layer to produce said product layer followed by removing said upper layer.

18. A process according to claim 15 wherein said separating and recovering in step 4 is carried out by solidifying said lower layer to produce said product layer followed by removing said upper layer.

* * * * *